United States Patent [19]

Langer et al.

[11] 4,202,340

[45] May 13, 1980

[54] METHOD AND APPARATUS FOR MONITORING HEART ACTIVITY, DETECTING ABNORMALITIES, AND CARDIOVERTING A MALFUNCTIONING HEART

[75] Inventors: Alois A. Langer, Pittsburgh; Marlin S. Heilman, Gibsonia, both of Pa.; Morton M. Mower, Baltimore, Md.; Mieczyslaw Mirowski, 2405 Velvet Valley Way, Owings Mills, Md. 21117

[73] Assignee: Mieczyslaw Mirowski, Owings Mills, Md.

[21] Appl. No.: 878,005

[22] Filed: Feb. 15, 1978

Related U.S. Application Data

[62] Division of Ser. No. 620,025, Sep. 30, 1975, abandoned.

[51] Int. Cl.$^2$ .............................................. A61N 1/36
[52] U.S. Cl. .................................. 128/419 D; 128/702
[58] Field of Search .................. 128/2.06 A, 2.06 B, 128/2.06 R, 2.1 Z, 419 D, 696, 702, 708, 709, 693, 901, 902

[56] References Cited

U.S. PATENT DOCUMENTS

| | | | |
|---|---|---|---|
| 3,352,300 | 11/1967 | Rose | 128/2.06 A |
| 3,587,563 | 6/1971 | Ragsdale | 128/2.06 A |
| 3,716,059 | 2/1973 | Welborn et al. | 128/419 D |
| 3,811,428 | 5/1974 | Van Horn et al. | 128/2.06 B |

OTHER PUBLICATIONS

Ottonello, "English Journal of Physics", vol. 7, No. 11, Nov. 1974, pp. 878-879.
Stratbucker et al., "Rocky Mountain Engineering Society," 1965, pp. 57-61.

*Primary Examiner*—William E. Kamm
*Attorney, Agent, or Firm*—Fleit & Jacobson

[57] ABSTRACT

Disclosed is a method and an apparatus for monitoring heart activity, for indicating or detecting abnormalities in such activity, and for taking corrective measures to return an arrhythmic heart to normal sinus rhythm. In one embodiment, monitoring and detecting are accomplished by developing a probability density function from ECG signals, or by sampling at least two portions of a probability density function. In another embodiment, a phase lock loop circuit is utilized to indicate fibrillation by the loop's inability to lock onto R—R interval signals. And in still another embodiment, cardiac electrodes are used to sense pulsatile impedance changes, absent in the presence of fibrillation. Also disclosed is a two-stage detector whose second stage is brought out of a stand-by state only after an arrhythmic condition is indicated by the first stage.

16 Claims, 21 Drawing Figures

METHOD AND APPARATUS FOR MONITORING HEART ACTIVITY, DETECTING ABNORMALITIES, AND CARDIOVERTING A MALFUNCTIONING HEART

REFERENCE TO RELATED APPLICATION

This is a division of U.S. application Ser. No. 620,025, filed on Sept. 30, 1975, and now abandoned. The subject matter from the parent application which is not embodied herein, is embodied in continuation-in-part U.S. application Ser. No. 878,006, filed on even date herewith.

BACKGROUND OF THE INVENTION

Ventricular fibrillation (VF) is a lethal cardiac arrhythmia for which the only known efficacious treatment is electrical countershock. A victim of VF outside of the hospital setting has little chance of survival since treatment must take place within a few minutes after the onset of the episode.

Fortunately, new techniques and devices are being devised to help deal with this life threatening condition. Among these are computer techniques which aid in the identification of high risk VF patients, anti-arrhythmic drugs which can prophylactically be administered to these patients, programs for wide-spread cardiopulmonary resuscitation training, and implantable devices which can automatically detect VF and deliver cardioverting countershocks.

"Cardioverting" or "cardioversion" as used herein is intended to encompass the correction of a number of arrhythmic heart conditions, both lethal and non-lethal. Those arrhythmic heart conditions include atrial tachycardia, atrial flutter, atrial fibrillation, junctional rhythms, ventricular tachycardia, ventricular flutter, ventricular fibrillation, and any other non-pacemaking related arrhythmic condition which may be corrected by applying electrical shocks to the heart. Obviously then, "defibrillation" is included in the term cardioversion as a method of applying electrical shocks to the heart to defibrillate fibrillating atria or fibrillating ventricles.

Many of the known techniques, such as defibrillation in a hospital setting or defibrillation by a paramedic as part of a resuscitation program, rely upon the human detection of VF. This detection has typically been accomplished by a trained operator interpreting an ECG from an oscilloscope tracing. However, there are situations where such an approach to reversing VF is impossible or impractical. There is accordingly a great need for an electronic device able to accurately detect VF or other life threatening arrhythmias from an input ECG where such a traditional approach is unfeasible. For example, an external defibrillator could be built with an interlock to its discharge switch so that a shock can be delivered only after the presence of VF has been confirmed by a detector receiving an ECG signal from the paddles. Such a defibrillator could safely be used by even an untrained operator.

With regard to the automatic implantable defibrillator, techniques have been developed which are generally acceptable for detecting VF and discriminating between life threatening arrhythmias and other cardiac malfunctions. Yet there is considerable room for improvement with regard to detecting and discriminating VF from other non-fatal arrhythmias. Accordingly, another use for such a detector as noted above would be in the fully-implantable automatic defibrillator.

Previous approaches to VF detection for implantable devices have had certain drawbacks. Fundamental questions, particularly important to an automatic implantable defibrillator, relate to potential failure modes, the risks to a patient should the device reach one of these failure modes, and specifically to whether failure should occur in a passive or an active manner. Considerations of failure modes in another field, for example, have led pacer manufacturers to design pacers to resort to fixed rate pacing, an active mode, should there be a sensing failure such as caused by interference. The risk of competing with the natural heartbeat has been judged less than the risk of potential inhibition when pacing is needed.

Similar principles apply to the automatic implantable defibrillator, though simple answers do not exist. An active mode failure would result in the delivery of a shock when none is necessary, an occurrence which could be particularly unpleasent to the patient. A passive mode failure, on the other hand, would inhibit the delivery of a necessary shock, and could result in death. Obviously, failures must be minimized, but they still must be considered. In this regard, it is believed preferable that potential sensing failures lead to inherent passivity of a defibrillating device.

In many known VF detectors and automatic implantable defibrillators, the primary detection schemes would result in active mode failures unless other lockout circuitry is provided. Examples are R-wave sensors, pressure sensors, and elastomeric contraction sensors. In each case a failure in the primary sensor would have the same inherent effect as fibrillation, causing the automatic implantable device to fire, an active failure.

There is accordingly a great need for a VF detector which is accurate in its detection of VF or other life threatening arrhythmias, so that failure modes may be passive. It is toward the development of a VF detector such as this that the present invention is directed. The present invention is directed more generally to the development of an accurate, simple detector of cardiac arrhythmias which overcomes or eliminates the drawbacks of known detectors.

SUMMARY OF THE INVENTION

The present invention relates to a system for measuring the electrical activity of the heart, and which can reliably discriminate between hemodynamically efficient and inefficient arrhythmias, being particularly sensitive to ventricular fibrillation. Though presented as a part of an automatic implantable defibrillator, it should be appreciated that the present invention is not limited to this specific application. For example, and as noted above, other arrhythmias or tachyarrhythmias can easily be identified by utilizing the teachings of the present invention.

Customarily, the term electrocardiogram (ECG) implies the use of electrodes on the body surface to obtain electrical signals indicative of heart activity. The term electrogram, on the other hand, generally refers to measurements made at the surface of the heart. As used herein, "ECG" is defined broadly, and refers to any measurement of the electrical activity of the heart, notwithstanding the source or technique of the measurement.

With the present invention, VF may be detected with a degree of accuracy never before possible, and hence inherent passive failure modes can be afforded. The inventive detector enjoys operation independent from the concepts of QRS detection and heart rate calculations to maximize accuracy. As is known, these concepts are particularly difficult to define during ventricular fibrillation. Furthermore, the present invention provides a technique for utilizing an ECG signal to derive substantially more information about heart function than has heretofore been possible.

In its first and most basic embodiment, the inventive VF detector depends for its operation upon the principle of probability density function. Briefly, the probability density function defines the fraction of time, on the average, that a given signal spends between two amplitude limits. It has been noted that the probability density function of an ECG changes markedly between ventricular fibrillation and normal cardiac rhythm. Accordingly, VF can be detected by providing a mechanism for generating a probability density function (or a portion thereof), or approximating one or more points on the function. The entire probability density function need not always be developed; rather, it is sometimes sufficient to develop only particular values of the function at certain sampling points.

In its first embodiment, the present invention relates to a method and a simple circuit for developing and utilizing an entire probability density function curve, or for developing the function, and sampling the same only at select points. In copending application Ser. No. 878,006, on the other hand, there is disclosed a simple circuit for detecting VF through the means of what can be thought of as approximating a probability density function at a single point, the ECG base line.

The present invention also relates to a VF detector which senses the regularity of the R-to-R interval. It has been observed that during high rate tachyarrhythmias (on the order of 250 beats per minute), R-waves can still be identified, and almost always occur at a stable rate. During fibrillation, on the other hand, there are no such regular R-waves. Accordingly, the present invention relates to a detector, preferably serving as a second-stage detector utilized with the probability density function detector discussed above, includes a phase lock loop circuit which monitors the variability in the R-to-R interval. The loop locks onto regularly occurring R-waves, but if the R-to-R interval becomes irregular, as in VF, the loop cannot lock. The present invention makes use of this inability to lock as evidence of fibrillation.

Further considered in the present invention is a VF detector in the form of an impedance sensor which measures impedance between cardiac electrodes. Preferably, this detector serves as a second-stage detector to verify a VF diagnosis from the inventive probability density function detector. It has been found that the impedance due to cardiac contractions is related to stroke volume. During fibrillation, stroke volume goes substantially to zero, and a severe drop in pulsatile impedance change can be detected as indicative of VF.

The impedance sensor discussed above requires a relatively large input power to perform its sensing function. The present invention therefore also contemplates a circuit by which the impedance sensor remains in a stand-by low power state for the greater majority of time, and is fully enabled only upon its preceding detector stage sensing what is diagnosed to be VF.

It is accordingly the main object of the present invention to provide an accurate detector of cardiac activity.

Another object of the invention is to provide a method and apparatus for monitoring heart activity.

An added object of the invention is to provide a method and apparatus for monitoring heart activity, for detecting abnormalities, and for cardioverting a malfunctioning heart, when appropriate.

A further object of the present invention is to provide a system wherein a probability density function generated in dependence upon an ECG trace is utilized to provide information about cardiac activity.

Another object of the present invention is to provide a system utilizing the principle of probability density function for detecting ventricular fibrillation.

Still a further object of the present invention is to provide a phase lock loop detector for detecting cardiac arrhythmias.

Another object of the present invention is to provide a two-stage detector including a probability density function detector and a phase lock loop detector.

Another object of the present invention is to provide a system for detecting cardiac arrhythmias including an impedance sensing detector.

A further object of the present invention is to provide a two-stage VF detector using a probability density function detector and an impedance detector.

Still another object of the present invention is to provide a multi-stage system for detecting cardiac arrhythmias, wherein one stage is fully enabled only after a preceding stage has diagnosed an arrhythmia.

Another general object of the present invention is to provide a simple and yet reliable VF detector which, should it fail, fails in a passive mode.

These and other objects of the present invention, as well as many of the attendant advantages thereof, will become more readily apparent when reference is made to the following description, taken in conjunction with the accompanying drawings.

DETAILED DESCRIPTION OF THE DRAWINGS

The probability density function cardiac arrhythmia detector forming a part of the present invention will first be described. However, before embarking upon a detailed explanation of the inventive circuit, there follows a brief discussion of the theory of probability density.

Figure 1A:
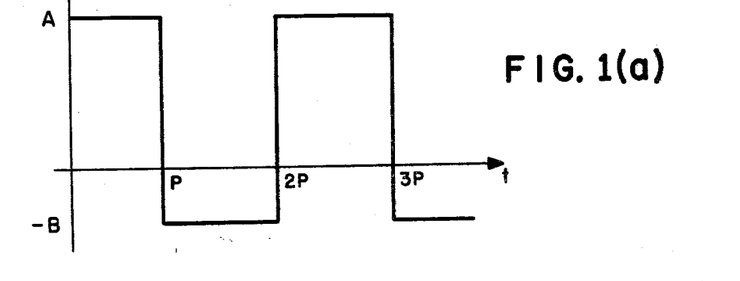
FIG. 1(a) is a tracing of a square wave given for exemplary purposes.
Figure 1B:
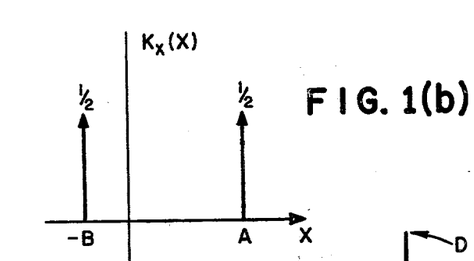
FIG. 1(b) is a plot of the probability density function of the wave illustrated in FIG. 1(a)

The inventive detector system is based upon a series of measurements on the ECG. The measurements are known in the literature as the probability density function, denoted as $K_x(X)$. If $X(t)$ is a function of time, then $K_x(X)$ can be interpreted as a function that defines the fraction of time, on the average, that $X(t)$ spends between two limits. For example, the area under $K_x(X)$ between $X=X_1$ and $X=X_2$ is the fraction of time that $X(t)$ spends between the limits $X_1$ and $X_2$. Looking at the simplified example illustrated in FIG. 1(a), it can be seen that $X(t)$ is always either at the levels $X=-B$ or $X=A$, and that the waveform spends half of its time at each one of these limits. The probability density function for this example is illustrated in FIG. 1(b), wherein the continuous function of time $X(t)$ has been mapped into a function of the amplitude-time distribution of $X(t)$.

In developing the present invention, it was recognized that the shape of 1 probability density function of an ECG changes markedly between normal cardiac rhythm and ventricular fibrillation. In this regard, the attention of the reader is directed to FIG. 2(a) which illustrates a typical ECG trace, to FIG. 2(b) which shows the probability density function of the ECG illustrated in FIG. 2(a), to FIG. 3(a) which illustrates an exemplary ECG trace representing ventricular fibrillation, and to FIG. 3(b) which is the probability density function of the trace illustrated in FIG. 3(a). It will be noted that when comparing normal cardiac rhythm with ventricular fibrillation, the greatest changes occur in the respective ECG traces at $X=0$, or at the baseline of the ECG signal. This is markedly reflected in the probability density functions as can be seen when contrasting FIGS. 2(b) and 3(b).

In the most simplified embodiment of the present invention, as is more fully described in the aforementioned copending application Ser. No. 878,006, an approximation of the probability density is developed for one value of X, namely $X=0$ or at the baseline of a filtered ECG. It should be noted that many other sampling levels are available for X other than zero, as will be explained below, and hence the number or level of sampling points are not in any way intended to be limited.

The probability density function provides another tool for viewing the original time-amplitude function. All of the discrete characteristics of the original signal are retained, but are displayed in a different format. Thus information of general diagnostic significance is inherent in the presentation and in some instances can more readily be seen or measured automatically. The attention of the reader is therefore directed to FIG. 4, which illustrates a circuit, in greatly simplified block form, which can be used to provide complete displays of probability density functions. These traces of probability density provide a great deal of information in the detection and study of tachyarrhythmias.

Figure 4:
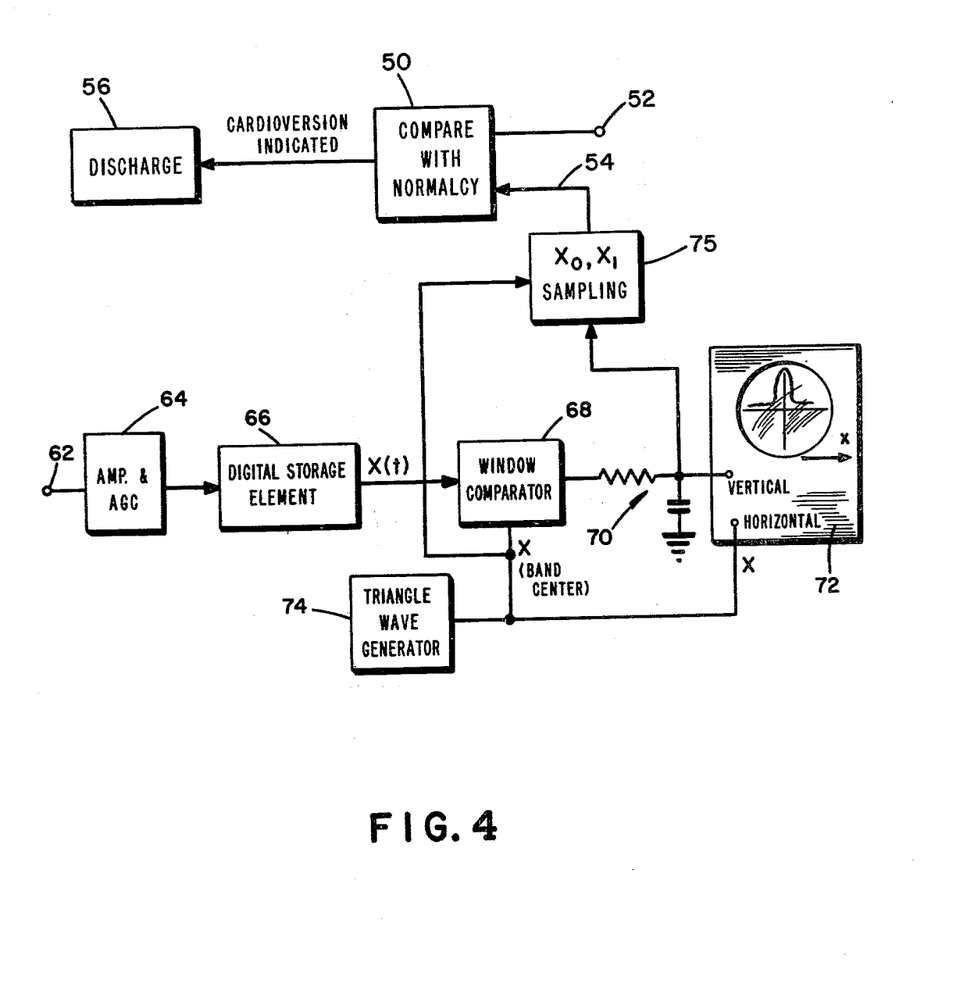
FIG. 4 is a block diagram of a circuit for developing probability density function traces for the input of an oscilloscope and/or for providing a sampling function.

In FIG. 4, an input signal is introduced at input terminal 62, to then be passed through an automatic gain control circuit 64. In this manner, input signals of different amplitude can be handled by the overall circuit. On the probability density display, signal amplitude appears on the abscissa, and therefore, AGC will normalize the width of the display.

A digital storage element 66 follows AGC circuit 64, and serves to provide a repetitive source of the input signal. The storage element 66 stores approximately two seconds of ECG data in a digital memory, and continually repeats this data. In this manner, the same data is repeatedly provided to a window comparator 68.

The window comparator 68 provides a logical "1" whenever its input signal lies within a narrow band centered around a band center "X". Then, by passing the output of the window comparator 68 through a simple low-pass filter 70, a voltage is developed which is proportional to the average time that the input stays within the designated band. This signal is fed to the "vertical" input of oscilloscope 72. And this is precisely analogous to the definition of the distribution as defined above. Slowly sweeping the band center "X" through the range of the input signal by means of a wave generator 74, provides a continuous display on the oscilloscope screen. The band center is coupled into the "horizontal" input of the oscilloscope 72.

Figure 2A:
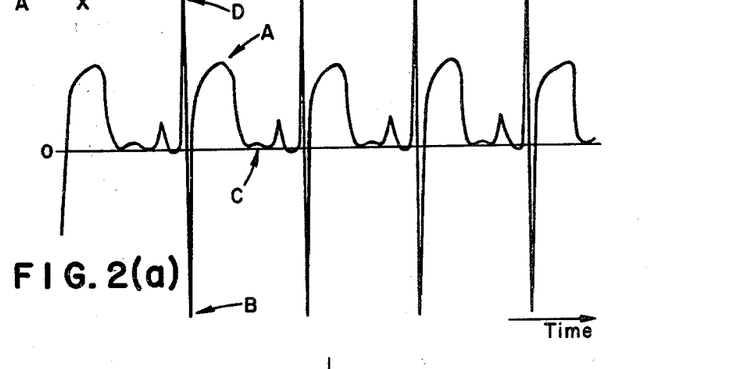
FIG. 2(a) is a typical catheter-sensed ECG trace.
Figure 2B:
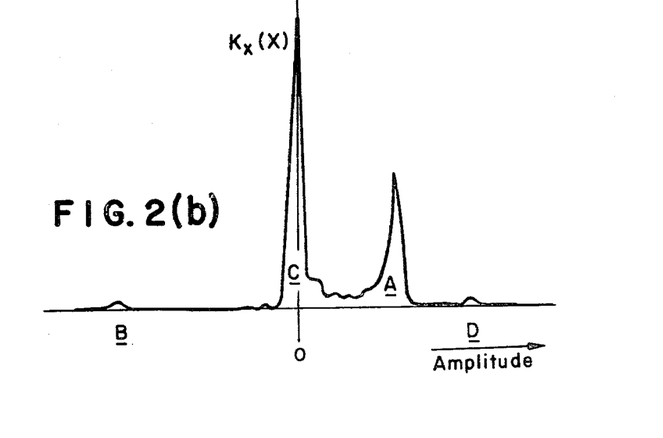
FIG. 2(b) is a plot of the probability density function of the ECG trace illustrated in FIG. 2(a)
Figure 3A:
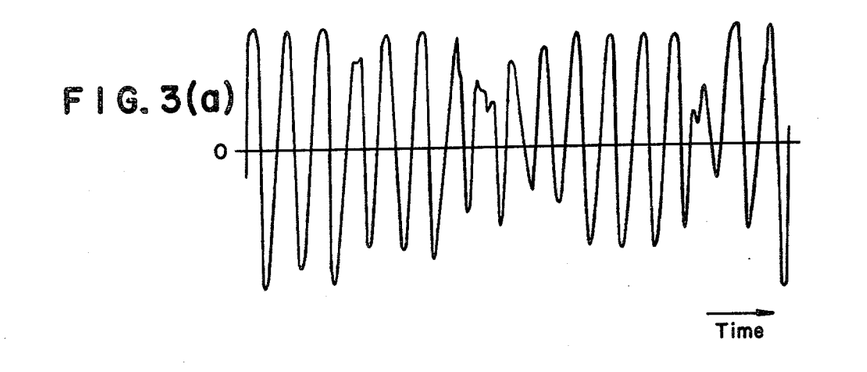
FIG. 3(a) is an ECG trace representing ventricular fibrillation.
Figure 3B:
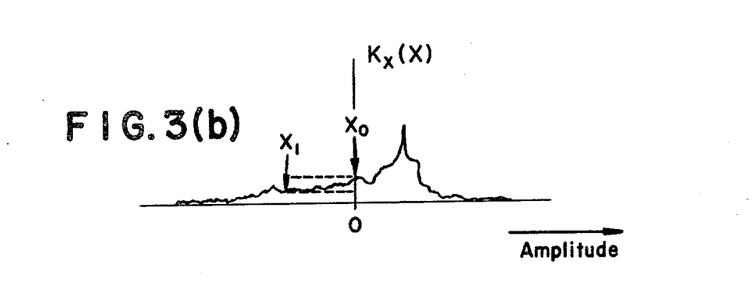
FIG. 3(b) is a curve representing the probability density function of the ECG trace illustrated in FIG. 3(a)

The respective traces of FIGS. 2(b) and 3(b) were developed from the circuit illustrated in FIG. 4. The trace of FIG. 2(a), as noted above, represents an electrogram recorded from an intracardiac catheter. The corresponding density function is shown in FIG. 2(b). Several regions have been identified on the respective traces, representing the same cardiac events but on the two different display patterns. For example, the region "B" of FIG. 2(a) is the most negative peak of the R-wave. The signal spends very little time at this value, thus the corresponding peak of the probability density curve of FIG. 2(b) is small. The peak at "A" is representative of the ST segment, and as is readily seen, the ECG signal spends more time on the average at this level than at region "B". Accordingly, the peak is higher at "A" in FIG. 2(b). The ECG dwells longest at the baseline identified at "C" in FIG. 2(a), and the zero peak is hence the largest in FIG. 2(b). FIGS. 2(a) and 2(b) also show an ECG peak at "D", and the correspondence of this peak on the probability density function curve. In accordance with the teachings of the present invention, the absence of a peak at zero in the probability density function is used as being characteristic of abnormal cardiac rhythm.

As mentioned previously, it is possible to detect VF by sampling points on a probability density function, rather than by developing and monitoring the entire function. For example, if two sampling points, say $X_1$ and $X_0$, are defined as shown in FIG. 3(b), more discrimination resolution becomes available by taking a ratio. As illustrated, approximate measurement at these two points on the waveform for this example would show the value of the probability density function to be:

For Normal Rhythm $$K_x(X_1) = .012 \qquad K_x(X_0) = 2.5$$

$$C_m = \frac{K_x(X_1)}{K_x(X_0)} = \frac{.012}{2.5}$$

$$C_m = .0048$$

For Ventricular Fibrillation $$K_x(X_1) = 0.8 \qquad K_x(X_0) = .11$$

$$C_m = \frac{K_x(X_1)}{K_x(X_0)} = .72$$

It can readily be seen that this measure yields over two orders of magnitude difference between normal cardiac rhythm and fibrillation. Sensing a value of $C_m$ near 1.0 corresponds to the detection of a severe arrhythmia. Sampling at two portions of the probability density function is indicated in FIG. 4 at 75.

With continuing reference to FIG. 4, it can be seen that the monitored probability density function can be used to initiate the discharge of energy into a needy heart. Although illustrated only in connection with $X_0$ and $X_1$ sampling, cardioversion can be controlled through the portion of the monitoring circuit which develops the complete probability density function.

In FIG. 4, a known input signal, corresponding to a normal probability density, is introduced to a comparator 50 at lead 52. The remaining input 54 to comparator 50 receives signals from $X_0$, $X_1$ sampler 75. If the input from sampler 75 is normal, then comparator 50 remains idle. If, on the other hand, a condition in need of cardioversion is indicated, comparator 50 issues a "cardioversion indicated" signal, and discharge of electrical energy into the heart is effected by discharge unit 56.

In view of the high degree of reliability necessary for the successful application of an implantable automatic defibrillator, it may become desirable to improve the accuracy of the detection system even relative to that described immediately above. This can be done by adding stages of sensing devices responsive to other parameters. One such parameter which can aid in the discrimination of very severe tachyarrhythmias and fibrillation is the variability in the R-to-R interval. As noted above, even during extremely high-rate tachyarrhythmias, R-waves can be identified and generally occur at a stable rate. During fibrillation, on the other hand, all regularity in the R-waves is lost. It is therefore possible to discriminate between fibrillation and tachyarrythmias by monitoring the regularity of the R-wave intervals by means of an R-wave detector.

In this latter regard, the present invention relates to the technique of ascertaining R-to-R interval variability by way of a phase lock loop circuit. The phase lock loop circuit has the capability of "locking" onto periodic input signals and providing an AC output voltage which is at a constant phase and at a frequency which is an integral multiple of the input frequency. If the input is not periodic, however, the loop cannot "lock", and this condition is easily detected. Accordingly, the inability of the phase lock loop circuit to lock can be utilized to derive useful information.

By utilizing the probability density function detector as a first detector stage and a phase lock loop detector as a second detector stage, the absence of a locked stage in the phase lock loop detector, coupled with the condition of the first detector stage having issued a fibrillation output, verifies the presence of VF with an exceedingly high degree of accuracy. Phase lock loop circuits are well known in the literature, and an example of a low-power version with lock indication, directly applicable to fibrillation detection, can be found in Application Note ICAN-6101, RCA COS/MOS Integrated Circuits, 1975 Databook Series, pp. 471-478. Accordingly, the phase lock loop circuitry employed in the present invention is shown only in block form in FIG. 5. Its application to a fibrillation detector, and the use of inability to lock to derive information are, however, novel concepts.

Figure 5:
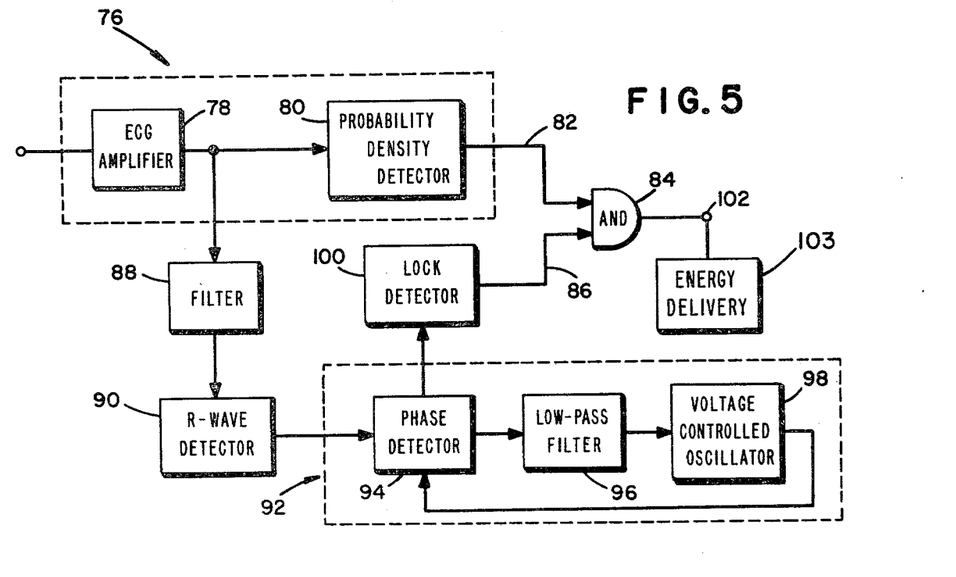
FIG. 5 is a block diagram of the inventive phase lock loop detector, shown as a second-stage detector used in conjunction with a probability density function detector.

With reference now to FIG. 5 and FIGS. 6(a)-6(f), the inventive use of a phase lock loop circuit in a fibrillation detection system will be described. Although the phase lock loop detector can alone be used to detect VF, it is illustrated in FIG. 5 as a second-stage of a VF detector. In FIG. 5, the previously-discussed probability density function fibrillation detector is illustrated as an integral part of a first stage detector shown at 76. The input to the first stage detector 76 reaches an ECG amplifier 78, and is processed by the probability density function detector 80. If fibrillation is sensed by the detector 80, then a signal is issued at line 82, and is fed to one terminal of an AND gate 84. The second input terminal 86 of AND gate 84 is associated with the second stage of the inventive detector combination, and in particular, the phase lock loop circuit shown generally at 92.

Figures 6A, 6B:
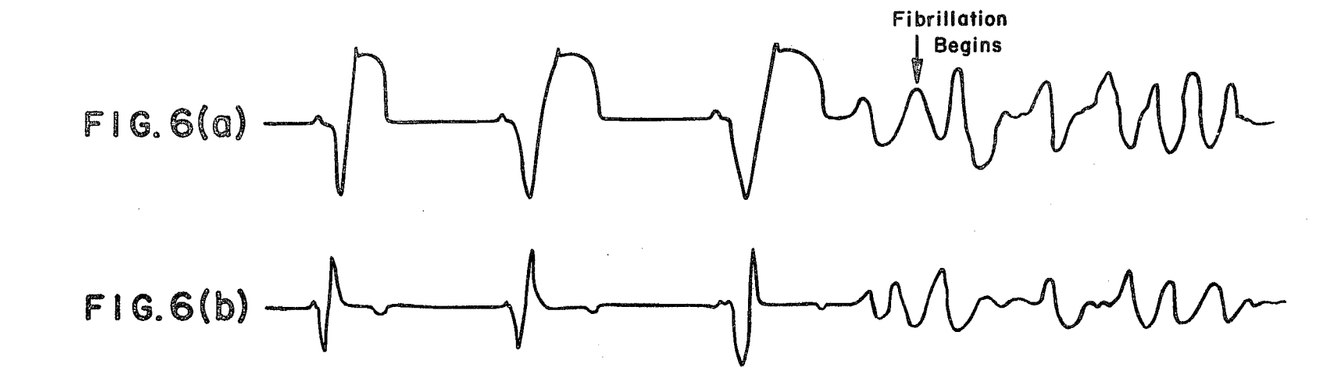
FIGS. 6(a) through 6(f) represent signals at select locations in the circuit illustrated in FIG. 5.

The signal issued by the ECG amplifier 78 also serves as an input to a filter 88 which feeds filtered signals to an R-wave detector 90, each being of conventional design. The ECG signal to filter 88 is illustrated in FIG. 6(a), while the filtered signal serving as the input to the R-wave detector 90 is shown in FIG. 6(b).

Figure 6C:
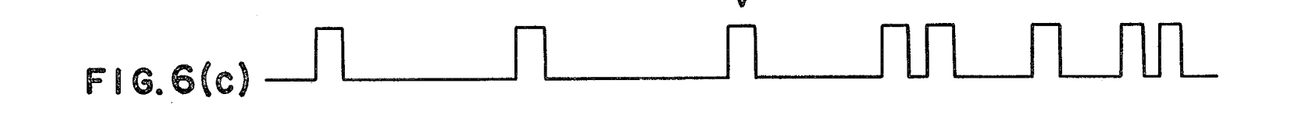

The R-wave detector 90 senses the presence of R-waves, and for each R-wave, issues a pulse of finite period. If the R-waves are regular in interval, the output of the R-wave detector 90 is a periodic train of pulses. FIG. 6(c) illustrates the output of the R-wave detector 90 based upon the input of the filtered ECG shown in FIG. 6(b). It will be noted that the first three pulses of R-wave detector 90 are periodic.

The phase lock loop circuit 92 includes a phase detector 94, the output of which is filtered by a low-pass filter 96, in turn feeding signals to the control side of a voltage controlled oscillator 98. The oscillator 98 issues a regular train of square wave pulses and feeds the same to the phase detector 94, which then compares the phase of these regular pulses with the input from the R-wave detector 90.

The phase lock loop 92 may be of numerous designs, as these circuits are well known. In any event, it is contemplated in the present invention that the phase detector 94 provide output information for a lock detector 100 which is indicative of the phase relationship between the R-wave detector pulses and the oscillator pulses, and in turn, which indicates whether the phase lock loop 92 is able to lock onto the input from the R-wave detector 90.

Figure 6D:
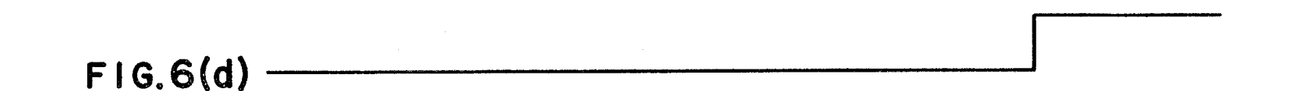
Figure 6E:
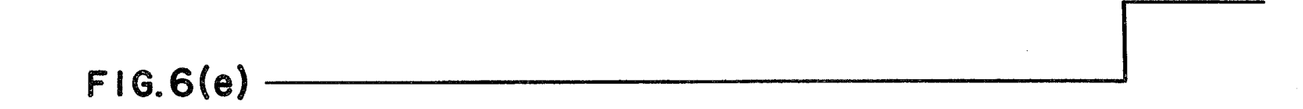
Figure 6F:
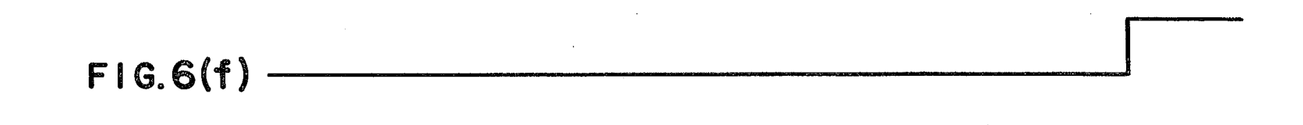

Upon the lock detector 100 receiving an indication from the phase detector 94 that the loop is locked, the detector 100 will, for example, issue a logical "0". Under this set of conditions, the AND gate 84 will remain idle, even if the probability density detector 80 has indicated on lead 82 that fibrillation is present. On the other hand, if the lock detector 100 receives a signal indicating that the loop 92 is not locked, then a logical "1" will be issued to AND gate 84, and if the logical "1" occurs simultaneously with a similar signal from the probability density detector 80, then the AND gate 84 will issue a signal on line 102 which will trigger the defibrillating electronics and actuate an energy delivery mechanism 103. Still, however, if the phase lock loop 92 cannot lock, and yet the probability density detector 80 has sensed no irregularity, then the AND gate 84 will remain idle. This is illustrated in FIGS. 6(d) through 6(f). FIG. 6(d) shows the output of the probability density function detector 80, FIG. 6(e) represents the output of the lock detector 100, and FIG. 6(f) represents the output of the AND gate 84 at lead 102.

As noted above, the phase lock loop circuit has before been used in cardiac applications. Typically, the loop is designed to lock onto the R-wave signals, even if such signals vary over wide ranges of input conditions. See, for example, the Van Horn et al U.S. Pat. No. 3,811,428. There, the phase lock loop circuit is used to lock onto fetal R-waves so that even during such times when the fetal heart beat is masked by the maternal heart beat, it is possible to provide an indication of predicted fetal beat. With the present invention, for the first time, the inability of a phase lock loop circuit to lock provides useful information; when the circuit is unable to lock, VF is indicated, and appropriate action is then taken.

Now, the inventive impedance sensor VF detection circuit will be described. It has already been proposed to use intraventricular pressure as an input variable to a fibrillation sensor. See U.S. Pat. Nos. Re. 27,757 and Re. 27,652, assigned to the present assignee. A drop in ventricular pressure corresponds to a life threatening arrhythmia, and this measurement is advantageous for it provides a direct indication of the life threatening condition, namely a loss of cardiac output. Unfortunately, long-term reliable pressure measurements are difficult to make. The inventive impedance detector is able to provide the same direct measurement of the life threatening arrhythmia, and is also capable of accurate long term utilization.

Figure 7:
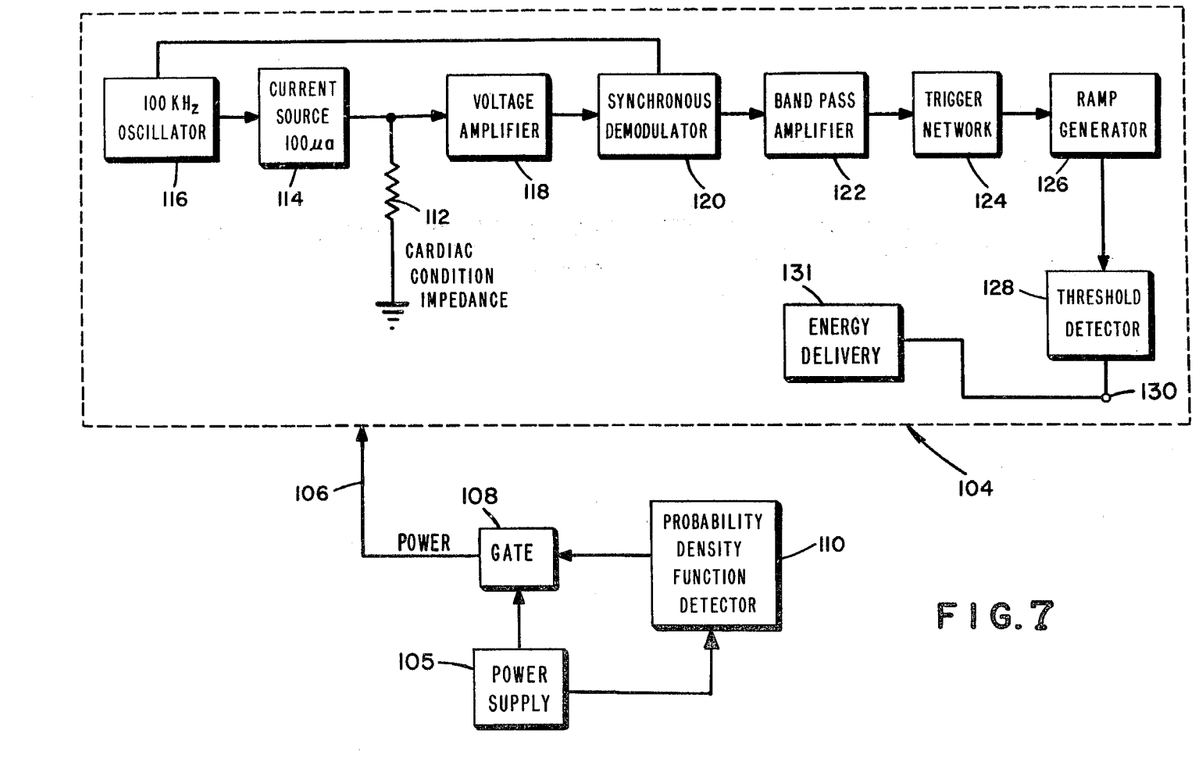
FIG. 7 is a block diagram of the inventive impedance sensor for detecting ventricular fibrillation, shown as a second-stage detector used in conjunction with a probability density function detector.

An electrical measurement which is easily and reliably made is the electrical impedance between two electrodes in or about the heart. It has been found that this impedance changes in accordance with cardiac contractions, and is directly related to stroke volume. That is, the impedance between cardiac electrodes varies in accordance with the volume of blood in the heart. When in normal rhythm, the heart regularly contracts and fills, and hence the normal impedance change is periodic. During fibrillation, however, stroke volume essentially goes to zero, and hence a severe drop in pulsatile impedance change can be seen. The inventive circuit illustrated in block form in FIG. 7 is able to detect the absence of pulsatile impedance changes, analogous to a drop in stroke volume, and hence ventricular pressure. The traces of FIGS. 8(a) through 8(f) relate to the circuit illustrated in FIG. 7.

With reference then to FIGS. 7 and 8, the inventive impedance VF detector is shown generally at 104. The detector 104 is powered by a power supply 105 on line 106, placed in the circuit by a gate 108 which is, in turn, controlled by the probability density function detector shown at 110. It is possible to utilize the impedance detector alone to recognize and respond to VF. However, as noted previously, the impedance VF detector requires a substantial amount of power from the implanted battery source. Therefore, so as not to drain the battery, the dector 104 preferably serves as a second-stage detector, and is so illustrated in FIG. 7. When used as a second-stage detector, the impedance detector 104 is designed to remain in a stand-by state until the probability density function detector 110 senses an abnormaility and triggers the impedance detector 104 by placing its power supply 105 into the impedance detector circuit 104 through the means of gate 108. In this way, the circuit of FIG. 7 provides an implied "AND" function. That is, the second-stage circuit 104, which triggers the defibrillating electronics, is only actuated upon command from the first-stage probability density function detector 110. Therefore both circuits must agree that fibrillation is present before a fibrillation output is generated.

The basic element in the impedance VF detector 104 is illustrated schematically as cardiac condition impedance 112. The impedance 112 is, for example, related to the impedance of the blood and tissue measured across intracardiac electrodes spaced apart on a catheter. A current source 114 associates with the impedance 112 and provides a current input of constant value. An oscillator 116 feeds the current source 114 so that source 114 generates an AC current to the impedance 112. In this manner, the voltage across the impedance 112 will be proportional to the current multiplied by the impedance value. As typical values, the oscillator 116 is set to 100 KHz, with the current source 114 supplying 100 μa. The impedance 112 is typically on the order of 50 ohms, and therefore approximately 5 mV appears across impedance 112. The voltage across the impedance 112 is then amplified by means of a voltage amplifier 118, and the amplified voltage from amplifier 118 is then demodulated by means of a synchronous demodulator 120.

The amplified and demodulated output of demodulator 120 is fed to a bandpass amplifier 122, and then to a trigger network 124, a ramp generator 126, and a threshold detector 128. The output of the threshold detector 128, if present, appears at terminal 130, and serves to trigger the defibrillation circuitry into operation; this is indicated by the energy delivery block 131.

Figure 8A:
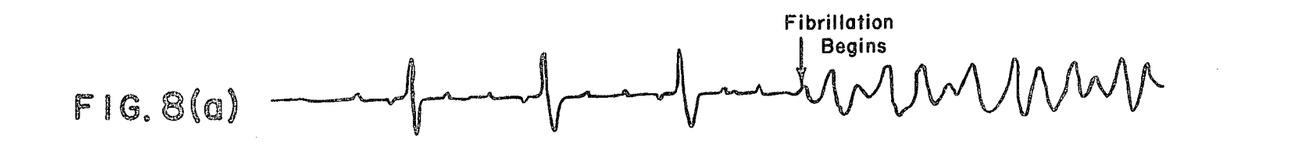
FIGS. 8(a) through 8(f) are traces for explaining the operation of the impedance detector illustrated in FIG. 7.
Figure 8B:
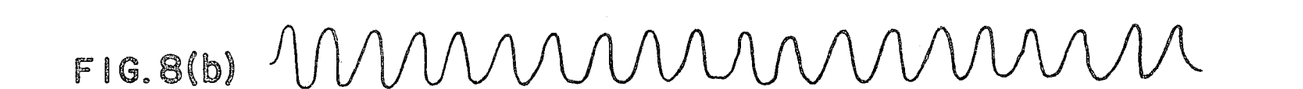
Figure 8C:
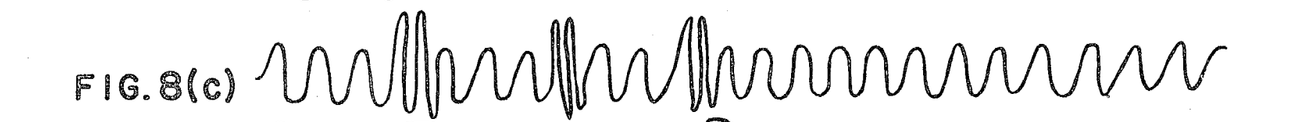

FIG. 8(a) represents an ECG which is at first normal, and which then indicates fibrillation; FIG. 8(b) shows, in an exaggerated form so as to appear on the same time scale, the output of oscillator 116; and FIG. 8(c) represents a trace of the voltage across impedance 112 after amplification by amplifier 118 and corresponding to the ECG in FIG. 8(a). It can be seen in FIG. 8(c) that the voltage across impedance 112 increases for each normal beat of the heart as blood is ejected from the heart.

Figure 8D:
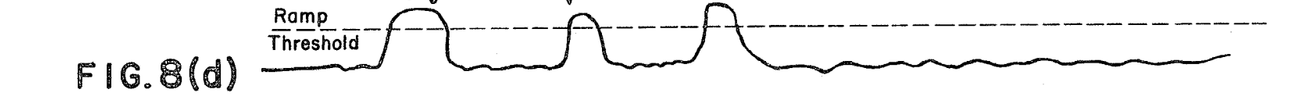
Figures 8E, 8F:
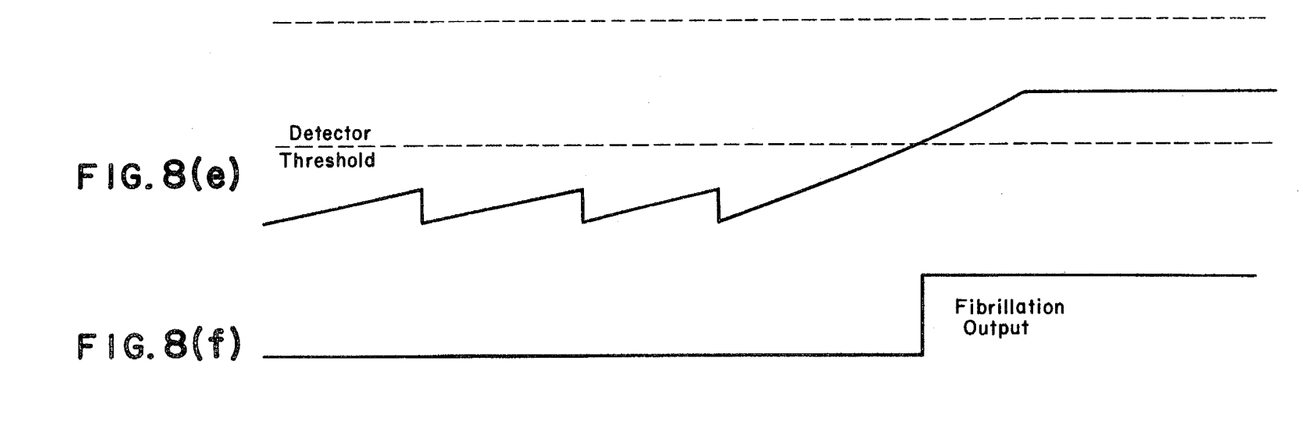

The output of demodulator 120, after amplification by amplifier 122, is illustrated in FIG. 8(d) where a negative-going signal is indicated for each reduction in voltage, or pulse, across impedance 112. Ramp generator 126 develops a ramp which is shown in FIG. 8(e). It will be noted that the ramp returns to its baseline each time the demodulated and amplified output of amplifier 122, represented in FIG. 8(c), crosses a set threshold level. Accordingly, during normal cardiac rhythm, the threshold detector 128 remains inactive. However, once fibrillation commences, where indicated in FIG. 8(a), the curve of FIG. 8(d) smoothes out, without the threshold being reached, and therefore the ramp of FIG. 8(e) continues to elevate until it exceeds the threshold of detector 128. At this occurrence, detector 128 is triggered, a fibrillation output is issued on line 130, and the energy delivery mechanism 131 is made to deliver a burt of energy to convert the arrhythmic heart to normal sinus rhythm.

Above, specific examples of the present invention have been described. It should be appreciated, however, that this description has been given for purposes of illustration only, and is in no way intended to limit the scope of the present invention. Rather, it is the intention that the present invention be limited only as defined in the appended claims.

What is claimed is:

1. A method for electronically monitoring the operation of a heart and for enabling the detection of abnormalities in cardiac function, the method comprising the steps of: sensing at least one cardiac parameter indicative of the operation of the heart being monitored; operating on the sensed cardiac parameter and generating a probability density function therefrom; and monitoring said probability density function by comparing the shape thereof with the shape of a probability density function indicative of normal cardiac function; wherein differences in shape between the normal probability density function and the probability density function generated from the heat being monitored, indicate abnormal cardiac function of the heart being monitored.

2. The method recited in claim 1, and further for reacting to abnormal cardiac functions, the method further comprising the steps of: cardioverting the heart if it is determined that the heart is in a state requiring cardioversion.

3. An apparatus for electronically monitoring the operation of a heart and for enabling the detection of abnormalities in cardiac function, the apparatus comprising: sensor means for sensing at least one cardiac parameter indicative of the operation of a heart being monitored; means for developing electrical signals representative of the sensed cardiac parameter; means for generating the probability density function of said electrical signals and; monitoring means for comparing the shape of the generated probability density function with the shape of a probability density function indicative of normal cardiac function; wherein differences in shape between the normal probability density function and the probability density function generated from the heart being monitored, indicate abnormal function of the heart being monitored.

4. The apparatus recited in claim 3, and having the further capability of cardioverting a heart upon the detection of a cardiac abnormality requiring cardioversion, the apparatus further comprising: means for issuing first cardioversion signals upon said monitoring means recognizing a condition requiring cardioversion; second-stage detector means for monitoring a cardiac parameter, for discriminating between normalcy in the monitored parameter and a cardiac state requiring cardioversion; and means for issuing second cardioversion signals upon said second-stage detector means recognizing a state requiring cardioversion; energy delivery means for delivering cardioverting energy to a heart; and means for actuating said energy delivery means only upon the issuance of both said first and said second cardioversion signals.

5. The apparatus recited in claim 4, wherein said second-stage detector means is an impedance detector which senses pulsatile changes of impedance between two cardiac electrodes.

6. The apparatus recited in claim 5, and further comprising: means for actuating said second-stage detector means only upon said first-stage detector means issuing a cardioversion signal.

7. The apparatus recited in claim 4, and further comprising: a phase lock loop circuit for attempting to lock onto R waves; wherein irregularity of the R-to-R interval during certain arrhythmias is indicated by the inability of the phase lock loop to lock onto R waves; and wherein said second cardioversion signals are issued when the phase lock loop is unable to lock onto R waves.

8. An apparatus for sensing the operation of a heart and for cardioverting a heart experiencing certain abnormal cardiac functions, the apparatus comprising: sensor means for sensing ECG signals of a heart; operator means for operating on the sensed ECG signals and for developing at least two portions of a probability density function thereof; discriminator means for comparing the shape of the developed probability density function with the shape of a known probability density function, and for discriminating between normalcy of said developed probability density function and a developed probability density function which is indicative of the need for cardioversion; and means for discharging cardioverting energy into the heart upon the sensing of a need for cardioversion.

9. The apparatus recited in claim 8, and further comprising means for indicating the need for cardioversion if the detected probability density function fails to correspond with said normal probability density function.

10. The apparatus recited in claim 8, wherein said operator means comprises a window comparator.

11. A two-stage apparatus for cardioverting a malfunctioning heart in such a manner that power is conserved, the apparatus comprising: first-stage detector means for discriminating between a normal cardiac state and a state requiring cardioversion; powering means for continually powering said first-stage detector means; second-stage detector means for further discriminating between a normal cardiac state and a state requiring cardioversion, normally in a stand-by condition and going to an active full power sensing condition upon initiation by said first-stage detector means; means for enabling said second-stage detector means and for thereby bringing said second-stage detector means from its stand-by condition to its full power active sensing condition; control means for powering said second-stage detector only upon said first-stage detector means sensing a cardiac state requiring cardioversion; delivery means for delivering cardioverting energy to the heart; and means for actuating said delivery means upon said second-stage detector means sensing a cardiac state requiring cardioversion.

12. The apparatus recited in claim 11, wherein said second-stage detector means is an impedance detector which senses the pulsatile changes of impedance between two cardiac electrodes; and further comprising means for discriminating between normalcy in the pulsatile changes and a cardiac condition requiring cardioversion.

13. The apparatus recited in claim 11, wherein said second-stage detector is normally in a low power stand-by condition.

14. An apparatus for cardioverting a needy heart, the apparatus comprising: sensor means for sensing the activity of a heart; means for generating electrical signals indicative of the R-to-R interval of said heart; phase lock loop circuitry for receiving and locking onto said electrical signals; sensing means for determining whether or not said phase lock loop circuitry has locked onto said electrical signals; delivery means for discharging cardioverting energy into said heart; means for issuing an enabling signal; and means for utilizing said enabling signal for initiating the discharge of cardioverting energy by said delivery means upon the sensing means determining the inability of said phase lock loop circuitry to lock onto said electrical signals.

15. A method for electronically monitoring and detecting abnormalities in cardiac function, the method comprising the steps of: sensing the electrical activity of a heart being monitored, and developing a cardiac parameter signal, such as an ECG, therefrom; operating on the cardiac parameter signal to develop at least two portions of a complete probability density function curve; deriving a measure of the shape of the probability density function curve by evaluating an indicator function based on measurements made on said portions of a complete probability density function curve; and monitoring the results of the indicator function by comparing the results to those derived from normal cardiac states to determine if the probability density function has a shape indicative of an abnormal cardiac state.

16. An apparatus for electronically monitoring and detecting abnormalities in cardiac function, the apparatus comprising: sensing means for sensing the electrical activity of a heart being monitored, and for developing a cardiac parameter signal, such as an ECG, therefrom; operating means for operating on the cardiac parameter signal to develop at least two portions of a complete probability density function curve; means for deriving a measure of the shape of the probability density function curve by evaluating an indicator function based on measurements made on said portions of a complete probability density function curve; and monitoring means for monitoring the results of the indicator function by comparing the results to those derived from normal cardiac states to determine if the probability density function has a shape indicative of an abnormal cardiac state.

* * * * *